United States Patent [19]
Baker, Jr. et al.

[11] Patent Number: 5,865,736
[45] Date of Patent: Feb. 2, 1999

[54] METHOD AND APPARATUS FOR NUISANCE ALARM REDUCTIONS

[75] Inventors: Clark R. Baker, Jr., Castro Valley; Richard D. Moshier, Sunnyvale; Thomas J. Yorkey, San Ramon, all of Calif.

[73] Assignee: Nellcor Puritan Bennett, Inc., Pleasanton, Calif.

[21] Appl. No.: 940,438

[22] Filed: Sep. 30, 1997

[51] Int. Cl.⁶ .................................................. A61B 5/00
[52] U.S. Cl. .......................................... 600/323; 600/508
[58] Field of Search ................................. 600/300, 301, 600/310, 322, 323, 324, 326, 336, 481, 500, 508, 515

[56] References Cited

U.S. PATENT DOCUMENTS 3,848,586  11/1974  Suzuki et al. ............................ 600/508
5,368,026  11/1994  Swedlow et al. ........................ 600/323

*Primary Examiner*—Michael Peffley
*Assistant Examiner*—Eric F. Winakur
*Attorney, Agent, or Firm*—Townsend and Townsend and Crew LLP

[57] ABSTRACT

A method and apparatus for controlling alarms in medical diagnostic apparatus where an alarm is generated when a measured value for a physiological parameter passes a threshold. The method determines both the amount of time the measured value is past the threshold, and the amount by which the threshold is passed. The alarm is inhibited based upon a combination of (1) the amount of time and (2) how much past the threshold the measured value is. Preferably, the combination is an integral or some function of an integral.

17 Claims, 5 Drawing Sheets

METHOD AND APPARATUS FOR NUISANCE ALARM REDUCTIONS

BACKGROUND OF THE INVENTION

The present invention relates to alarms in medical diagnostic apparatus, and in particular to reducing nuisance alarms for pulse oximeters.

A typical pulse oximeter measures two physiological parameters, percent oxygen saturation of blood hemoglobin (sat) and pulse rate (rate). For alarm purposes, low and high thresholds are set for both sat and rate, defining normal ranges within which it is desired to maintain the patient. For example, with a neonate it might be desired that sat should remain between 80 and 95 percent and rate should remain between 90 and 190 beats per minute. From the two measured parameters, four alarm types can be generated, low sat, high sat, low rate, and high rate. In a typical pulse oximeter, an alarm begins immediately when either sat or rate goes outside normal range and an alarm ends immediately when both sat and rate return within normal range. Alarms are typically announced by audible and/or visual indicators.

Each occurrence in which a measured parameter goes outside normal range is referred to as an event. Thus, in a typical oximeter, each event coincides with an alarm, and the alarm duration is identical to the event duration.

Many of the alarms produced by a typical oximeter are not generally considered to correspond to events which are clinically significant. The exact definition of clinical significance varies depending on the patient and circumstance, but is in general related to the severity and duration of the event of interest. For example, a very shallow desaturation might only be considered significant if sustained for a relatively long period of time. Likewise, a desaturation of very brief duration might only be considered significant if it falls very deep below the low sat threshold. In addition, parameter measurement error, due to noise or signal artifact, can produce false events. Any alarm that does not correspond to a clinically significant event is considered a nuisance alarm.

There have been published studies attempting to reduce the number of saturation alarms. These studies either looked at lowering the alarm threshold or waitinc some fixed period of time after the threshold was crossed. Lowering the threshold is problematic because a patient's saturation can remain indefinitely below the original threshold, but above the new threshold, and an alarm will never be generated. Delaying alarm generation by a fixed amount of time is also problematic due to the potentially serious situation in which a patient's saturation abruptly falls to and remains at a very low level, requiring prompt medical intervention.

SUMMARY OF THE INVENTION

The present invention provides a method and apparatus for controlling alarms in medical diagnostic apparatus where an alarm is generated when a measured value for a physiological parameter passes a threshold. The method determines both the amount of time the measured value is past the threshold, and the amount by which the threshold is passed. Alarms are inhibited based upon a combination of the amount of time and the amount by which the threshold is past. Preferably, the combination is an integral or some function of an integral.

For saturation alarms on a pulse oximeter, the preferred embodiment calculates the integral of the amount by which the oxygen saturation exceeds an upper threshold, or falls below a lower threshold. A saturation alarm is generated when the integral exceeds a predetermined value. Similarly, for rate alarms on a pulse oximeter, the preferred embodiment calculates the integral of the amount by which the pulse rate exceeds an upper or lower threshold, and a rate alarm is generated when the integral exceeds a predetermined value.

The present invention also provides a number of alternate embodiments. The integral function, used to inhibit alarm generation, can be modified to make the algorithm more or less sensitive to various types of events. Several example integral functions are presented, along with the corresponding effect on algorithm performance. The integral reset function, used to zero the integral, can be modified to adjust the hysteresis characteristic of the algorithm.

A basic embodiment is presented in which the integral and alarm are immediately cleared when the measured parameter returns to within normal range. Another embodiment, referred to as fading, is preferred for use with saturation alarms because it provides sensitivity to multiple closely spaced incursions. The fading embodiment does not immediately clear the integral when the measured parameter returns to within normal range, but rather gradually reduces it. Two additional embodiments are presented, one that puts greater emphasis on deep events, and another that anticipates where an event is going.

For a further understanding of the nature and advantages of the invention, reference should be made to the following description taken in conjunction with the accompanying drawings.

DESCRIPTION OF THE PREFERRED EMBODIMENT

The present invention relates to reducing alarms in medical diagnostic equipment measuring a physiological parameter. In order to illustrate the invention, the example of a pulse oximeter with thresholds for saturation will be described. In particular, a low saturation threshold is described. Alternately, high saturation, low pulse rate, high pulse rate or other alarm parameters could be addressed by the present invention. In addition, the invention could be used for other types of medical diagnostic equipment.

Figure 1:
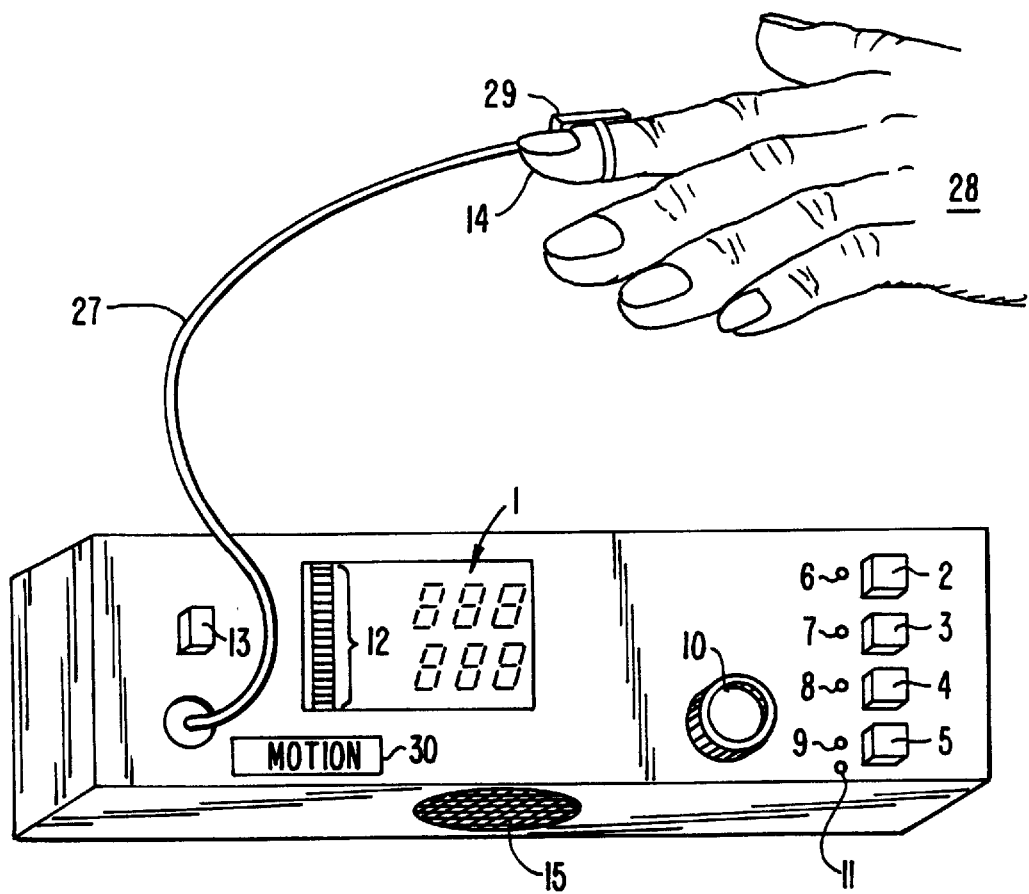
FIG. 1 is a diagram of an example pulse oximeter illustrating the alarm display.

FIG. 1 illustrates a typical pulse oximeter. FIG. 1 illustrates the oximeter housing, which includes a digital display circuit 1, circuitry select buttons 2–5, alarm status lights 6–9, and optically coupled adjustment knob 10, synchronization status light 11, LED digital view meter 12 and power switch 13. A connector 27 to the sensor 29 is shown with the sensor attached to a finger 14 on a patient's hand 28.

An alarm in accordance with the present invention can be either produced audibly through a speaker 15, or produced on one of the displays described above. Also shown is a display 30 for providing an indication of motion distorting the signal, which could also generate an alarm condition.

Figure 2:
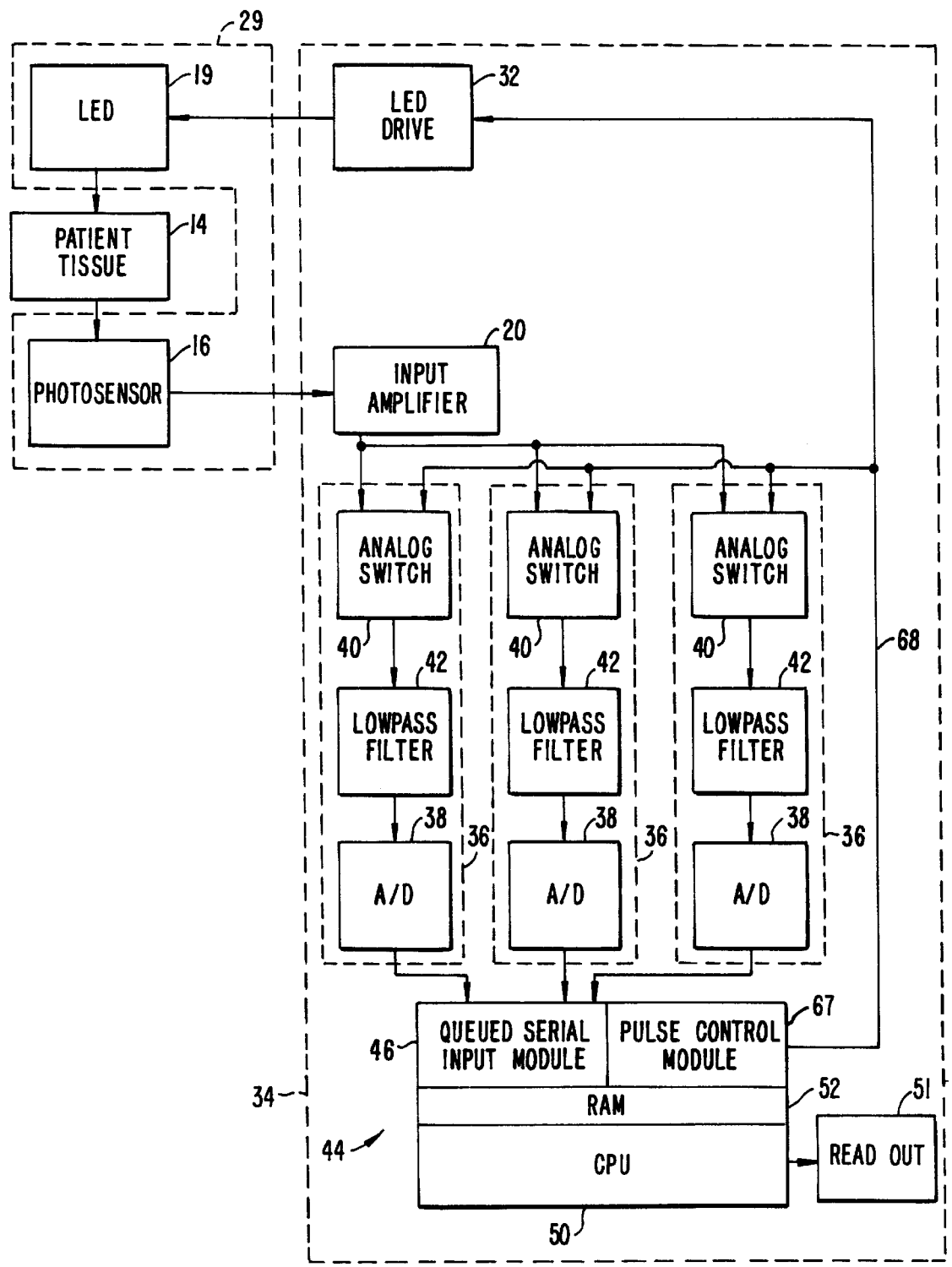
FIG. 2 is a block diagram of example pulse oximetry circuitry illustrating how measurements are made.

FIG. 2 is a block diagram of an example of electronic circuitry for a pulse oximeter incorporating the present invention. Shown is sensor 29 which includes LEDs 19 which provide light through patient tissue 14 to a photosensor 16. The LEDs are driven by a drive circuit 32 via a signal line 68 from a pulse control module 67. The signal from photosensor 16 is provided through input amplifier 20 to three possible channels 36. Each channel includes an analog switch 40, lowpass filter 42 and an A/D converter 38. The signals are provided to a queued serial input module 46, which provides data to a RAM 52 for reading and analysis by a CPU 50. The control circuitry is generally referred to as a microcontroller/processor unit (MPU) 44. A readout circuit 51 is also shown for providing outputs to one of the displays shown in FIG. 1 or to another output.

An algorithm according to one embodiment of the invention calculates the integral of the difference between the current saturation and a saturation threshold whenever the current saturation is below the saturation threshold. Because we are working with a sampled data system, we used a simple summation to approximate the integral.

$$I_{sat}(n) = I_{sat}(n-1) + |T_{sat} - sat(n)| \quad (1)$$

where Isat(n) is the saturation integral at time n, sat(n) is the saturation at time n, and Tsat is the saturation threshold. Those skilled in the art will recognize that an equivalent continuous-time form could also be used. An alarm is generated when $I_{sat}$ exceeds an integral threshold.

Figure 3:
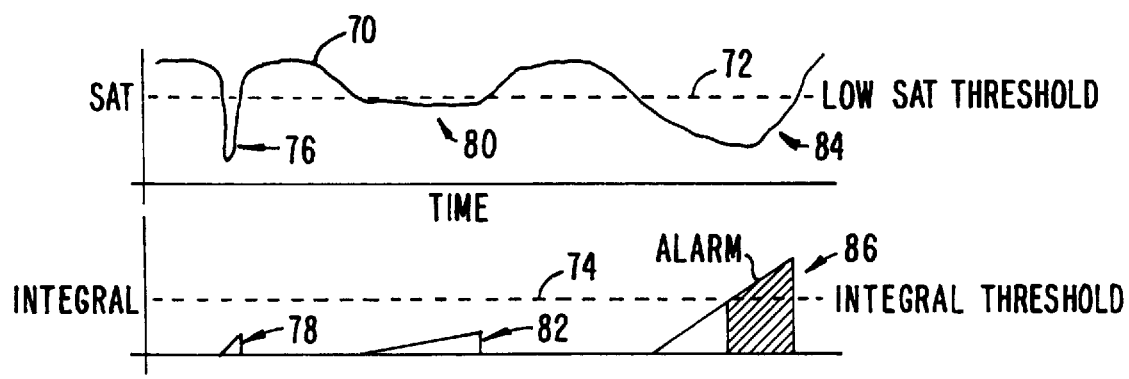
FIG. 3 is a graph illustrating the alarm response according to the present invention.

FIG. 3 illustrates the behavior of the integral algorithm. A saturation signal 70 is compared to a low sat threshold 72. Also illustrated is an integral threshold 74. As can be seen, three separate incursions below the low sat threshold are shown. A deep but short incursion 76 produces an integral value 78 which does not exceed the integral threshold 74, and thus does not produce an alarm. In prior devices, because the low sat threshold was passed, an alarm would have been generated even though the event is short lived and would thus be considered a nuisance-type alarm.

In a second example, an incursion 80 barely drops below the low sat threshold, but stays there for an amount of time. This would also cause a nuisance alarm in systems which immediately alarm on any incursion below the low sat threshold. In addition, prior art systems which produce an alarm after a fixed time for incursions below the low sat threshold will also produce an alarm when that time is exceeded. In the present invention, however, as illustrated by integral 82, the integral threshold is not exceeded because, although a significant amount of time passes, the incursion is limited.

A final incursion 84 is both long enough and deep enough to cause the integral value 86 to exceed the integral threshold and generate an alarm.

In implementing the alarm reduction algorithm, additional logic must be provided to govern when the integral equation is applied, how the integral is reset (i.e., zeroed), the integral/alarm relationship, and how the alarm is cleared. Upper and lower limits might be imposed on the integral. Integrals and/or alarms might be held until the measured parameter has been within normal range for a specified time duration and/or amount. Alternatively, an alarm might be cleared immediately when the measured parameter returns to normal range, but be regenerated immediately upon a subsequent event unless the parameter has been in normal range for a sufficient time duration and/or amount. The way these issues are handled affects the sensitivity and hysteresis of the algorithm. The preferred embodiment depends on the patient population of interest and the expected uncertainty inherent in the parameter estimation. We have examined two particular embodiments, which we will call the basic embodiment and the fading embodiment.

The basic embodiment integrates according to equation (1) while sat is abnormal, resets the integral when sat transitions from abnormal to normal, alarms when the integral reaches the integral threshold, and clears the alarm when sat transitions from abnormal to normal. With the basic embodiment, each event is treated as being distinct from all others.

Figure 4:
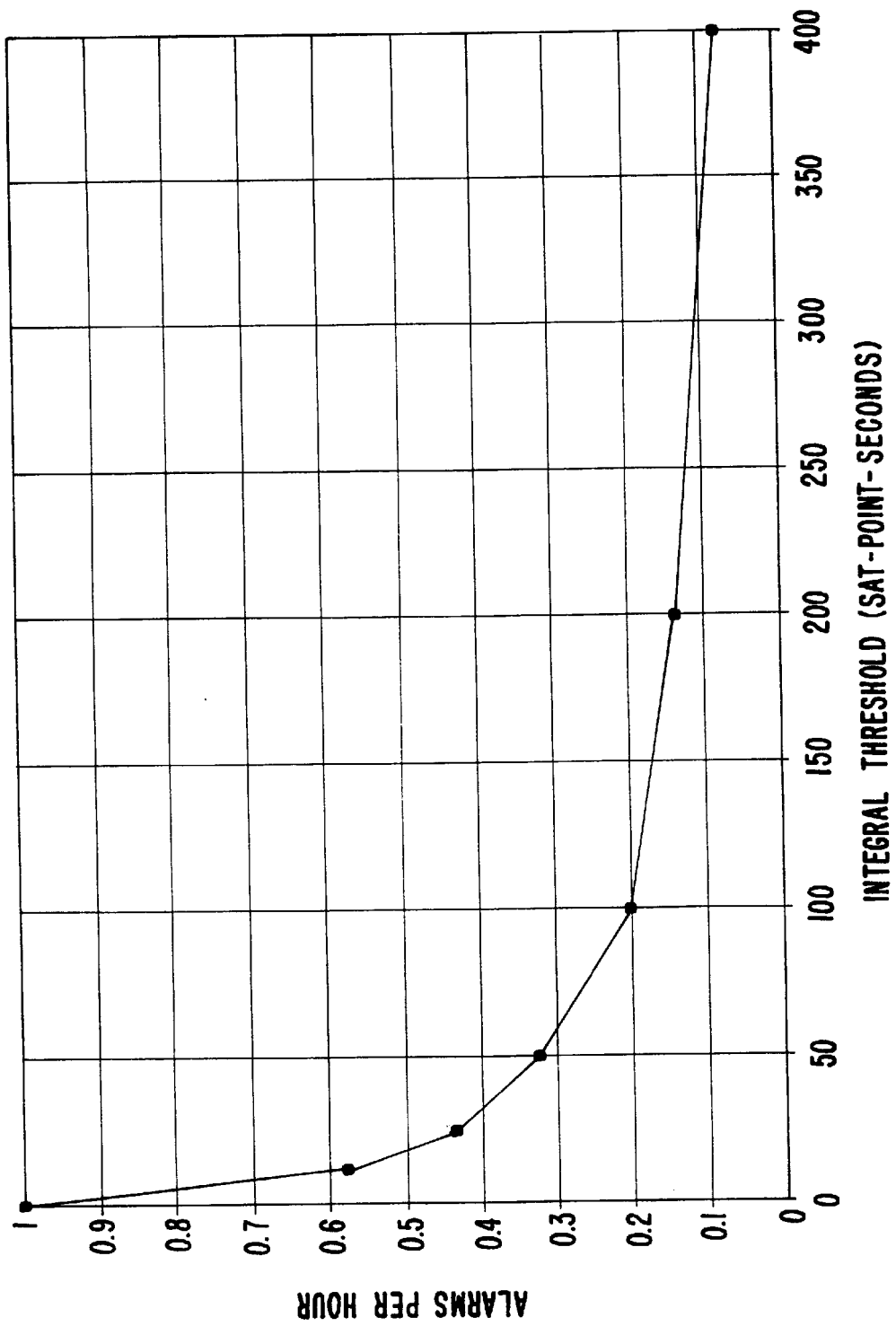
FIG. 4 is a graph illustrating the reduction in nuisance alarms with increasing integral delays according to the present invention.

FIG. 4 shows the reduction in alarms per hour with increasing integral threshold that is achieved with the basic embodiment. The alarms per hour have been normalized to one at an integral threshold of zero. The data in FIG. 4 was generated from a typical database of oximetry saturation files. Detailed analysis indicates that most of the eliminated alarms were nuisance alarms. As the integral threshold increases, a small number of alarms were eliminated that corresponded to events in which the true saturation would have met the clinical significance definition, but due to noise or artifact did not. Adjusting the integral threshold allows a tradeoff to be made between nuisance alarms, missed significant alarms, and the amount of alarm delay.

We have evaluated oximetry data from patient populations in which the basic embodiment may not be appropriate. These populations exhibit periodic desaturations in which it may not be appropriate to view each desaturation as a clinically separate event. For example, although a single incursion, similar to 76 or 80, should not generate an alarm, a sequence of such incursions occurring close together in time perhaps should generate an alarm. The preferred embodiment for these populations uses an integral clearing method that we refer to as fading. Fading is not an alarm reduction enhancement, but rather a means of obtaining sensitivity to periodic events.

The fading embodiment, as it pertains to saturation, works as follows. The integral is bounded with a lower limit of zero and an upper limit equal to the integral threshold value. When sat is outside normal range, the integral increases according to (1). When sat is inside normal range, the integral is reduced by the weighted difference between the sat and the low sat threshold, as shown in equation (2).

$$I_{sat}(n) = I_{sat}(n-1) - |W \times (T_{sat} - sat(n))| \quad (2)$$

The integral fading rate is controlled by w, which is typically a predetermined constant.

For the fading embodiment, the alarm is controlled by the integral value. An alarm state is defined in which an alarm sounds (or is otherwise indicated) when the alarm state is true and the alarm is quiet when the alarm state is false. If the alarm state is false, the alarm state is set to true when the integral reaches the integral threshold. If the alarm state is true, the alarm state is set to false when the integral reaches zero. Thus, the condition for clearing the alarm is that the fading integral (2) has reached zero.

Figure 5:
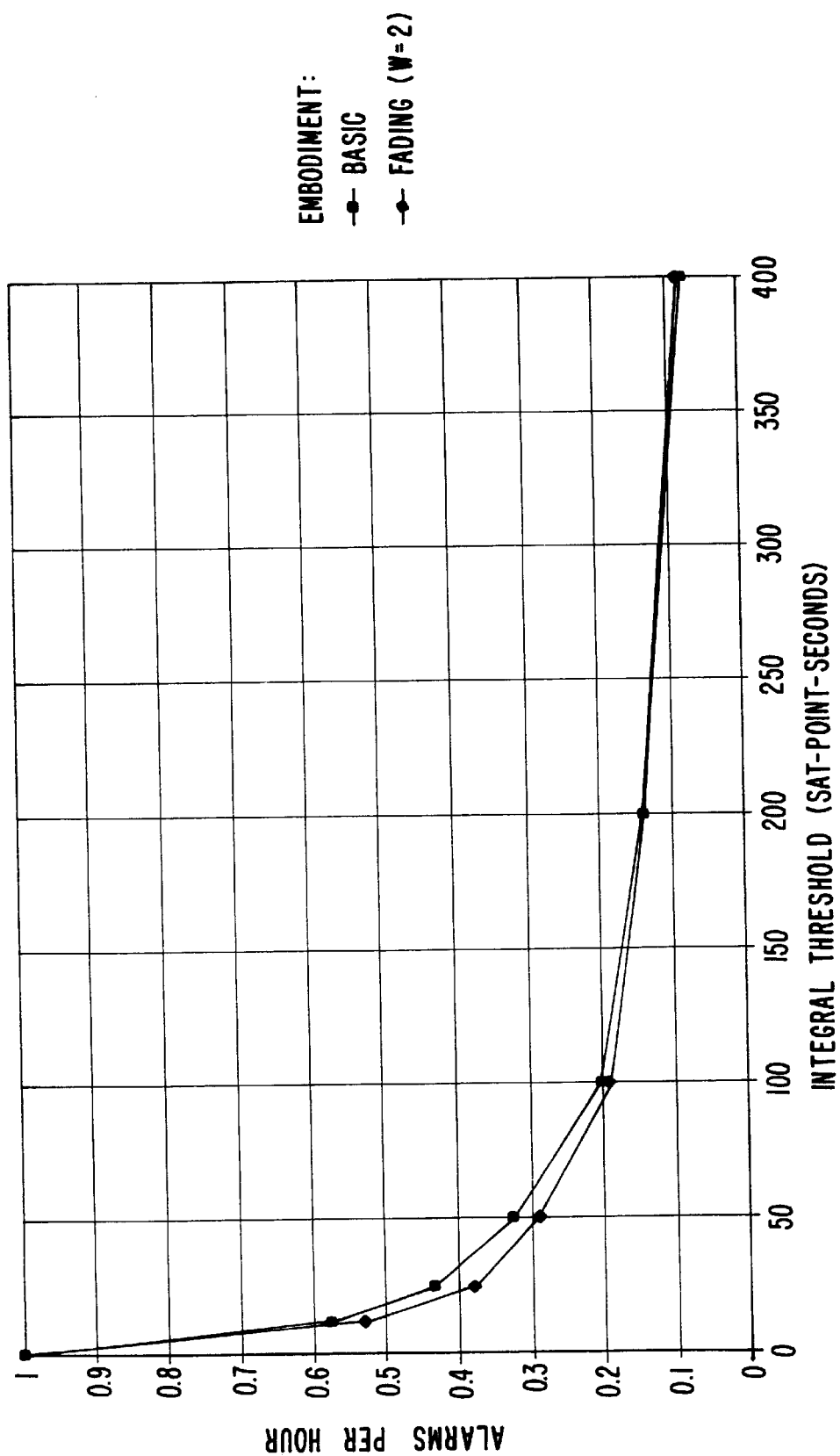
FIG. 5 is a graph illustrating the reduction in nuisance alarms using the integral method of the present invention and also using integral clearing, or fading.

We evaluated the fading embodiment on a clinical database containing periodic desaturation events. We chose an integral fading rate of twice that of the integral increase rate (i.e., w=2). We compared the performance of this fading embodiment with that of the basic embodiment. FIG. 5 shows that there is little difference in overall alarms per house (APH) vs. integral threshold for the two embodiments. The increase in APH due to new alarms introduced by fading is more than offset by a decrease in APH due to a merging of alarms that are separate in the basic embodiment. Alarm merging is possible when two alarming events occur close together in time. If the sat integral from the first alarming event has not faded to zero before the second alarming event begins, the two alarms merge into one.

Additional embodiments can be envisioned in which (1) is modified in order to alter the time responsiveness or sensitivity of the algorithm. For example, to increase responsiveness to deep desaturations, the square of the distance from the low sat threshold could be used, as shown in (3).

$$I_{sat}(n)=I_{sat}(n-1)+(\Delta sat(n))2 \qquad (3)$$

where: $\Delta sat=|T_{sat}-sat(n)|$

Other embodiments can be envisioned that use the slope of the saturation to anticipate where the saturation is going. One way to achieve this effect is to integrate faster when the saturation is falling and integrate slower when the saturation is rising. An equation that provides this effect is given in (4).

$$I_{sat}(n)=I_{sat}(n-1)+\Delta sat(n) \times a^{[sat(n-1)-sat(n)]} \qquad (4)$$

where: $a>1$ $\Delta sat=|T_{sat}-sat(n)|$

Another enhancement involves variable attack and decay rates. The idea here is to use one set of integration and fading rates before the alarm sounds and another set of rates after the alarm sounds.

We also used the integral method to screen pulse rate bradycardia and tachycardia alarms. The rate integral is calculated as a percentage in order to obtain a consistent alarm reduction effect, regardless of the rate threshold, $T_{rate}$.

$$I_{rate}(n) = I_{rate}(n-1) + 100 \times \left( \left| \frac{\text{rate}(n) - T_{rate}}{T_{rate}} \right| \right) \qquad (5)$$

where Irate(n) is the rate integral at time n, rate(n) is the rate at time n, and Trate is the rate threshold.

The alarm reduction method of this invention can be incorporated as an independent post-processing step that follows a saturation calculation algorithm. It is therefore suitable for use with existing pulse saturation algorithms.

As would be understood by those skilled in the art, the present invention may be embodied in other specific forms without departing from the spirit or essential characteristics thereof. For example, rather than an integral, some other function of the time and amount of an incursion could be used to control when an alarm is generated. An alarm can be considered inhibited according to an integral, or the alarm could simply have its generation controlled by the integral without anything being inhibited. The threshold itself could be considered partly a function of the integral, so it could be a moving threshold depending on an integral function of the variation in the measured quantity. Accordingly, the foregoing description is intended to be illustrative but not limiting, of the scope of the invention which is set forth in the following claims.

What is claimed is:

1. A method for controlling an alarm in a medical diagnostic apparatus, said apparatus generating said alarm when a measured value for a physiological parameter is outside a specified range, comprising the steps of:

determining a quantity of time said measured value is outside said range;

determining a measure of the amount by which said range is exceeded by said value for a plurality of times during said quantity of time; and controlling said alarm so no alarm is provided until a combination of said quantity of time and said amounts exceeds a predetermined level.

2. The method of claim 1 wherein said combination comprises an integral function.

3. The method of claim 1 wherein said measured value is an oxygen saturation, and said range is between a high oxygen-saturation threshold and a low oxygen-saturation threshold.

4. The method of claim 1 wherein said measured value is a pulse rate, and said range is between a high pulserate threshold and a low pulse-rate threshold.

5. The method of claim 1 further comprising the steps of:

clearing said alarm when said physiological parameter returns to within said range.

6. The method of claim 1 further comprising the step of:

clearing said alarm when a clearing condition is met, said clearing condition being a function of at least one of a time and an amount said value is within said range.

7. The method of claim 6 wherein said function provides that said alarm clears at a fading rate greater than a build-up rate.

8. A method for controlling an alarm in a medical diagnostic apparatus, said apparatus generating said alarm when a measured value for a physiological parameter is outside a specified range, comprising the steps of:

determining a quantity of time said measured value is outside said range;

determining a measure of the amount by which said range is exceeded by said measured value for a plurality of times during said quantity of time;

controlling said alarm so no alarm is provided until an integral function of said amount exceeds a predetermined level; and clearing said alarm when a clearing condition is met, said clearing condition being a function of at least one of a time and an amount said value is within said range.

9. A medical diagnostic apparatus, comprising:

a sensor for measuring values of a physiological parameter;

means for comparing said values to a range;

means for determining a quantity of time said measured value is outside said range;

means for determining an amount by which said range is exceeded by said values for a plurality of times during said quantity of time; and means for controlling said alarm so no alarm is generated until a combination of said quantity of time and said amount exceeds a predetermined level.

10. The apparatus of claim 9 wherein said combination comprises an integral.

11. The apparatus of claim 9 wherein said measured value is an oxygen saturation, and said range is between a high oxygen-saturation threshold and a low oxygensaturation threshold.

12. The apparatus of claim 9 wherein said measured value is a pulse rate, and said range is between a high pulserate threshold and a low pulse-rate threshold.

13. The apparatus of claim 9 further comprising:

means for clearing said alarm when said physiological parameter returns to within said range.

14. The apparatus of claim 9 further comprising:

means for clearing said alarm when a clearing condition is met, said clearing condition being a function of at least one of a time and an amount said value is within said range.

15. The apparatus of claim 14 wherein said function provides that said alarm clears at a fading rate greater than a build-up rate.

16. A medical diagnostic apparatus, comprising:

a sensor for measuring values of a physiological parameter;

means for comparing said values to a range;

means for determining a quantity of time said measured value is outside said range;

means for determining an amount by which said range is exceeded for a plurality of times during said quantity of time;

means for controlling said alarm so no alarm is provided until an integral function of said amount exceeds a predetermined level; and means for clearing said alarm when a clearing condition is met, said clearing condition being a function of at least one of a time and an amount said value is within said range.

17. A medical diagnostic apparatus, comprising:

a sensor for measuring values of a physiological parameter;

an alarm generator for generating an alarm to a user;

a processor for processing said values;

a memory for storing a program for said processor, said memory including instructions for comparing said values to a range;

determining a quantity of time said measured value is outside said range;

determining an amount by which said range is exceeded for a plurality of times during said quantity of time;

controlling said alarm so no alarm is generated until an integral function of said amount exceeds a predetermined level; and clearing said alarm when a clearing condition is met, said clearing condition being a function of at least one of a time and an amount said value is within said range.

* * * * *